US00PP14598P29

(12) United States Plant Patent
Cascante

(10) Patent No.: US PP14,598 P2
(45) Date of Patent: Mar. 16, 2004

(54) DOUBLE IMPATIENS PLANT NAMED 'CAMEO SCARLET SURPRISE'

(50) Latin Name: *Impatiens walleriana*
Varietal Denomination: Cameo Scarlet Surprise

(75) Inventor: Xenia Cascante, Alajuela (CR)

(73) Assignee: Oglevee Ltd., Connellsville, PA (US)

( * ) Notice: Subject to any disclaimer, the term of this patent is extended or adjusted under 35 U.S.C. 154(b) by 0 days.

(21) Appl. No.: 10/313,122

(22) Filed: Dec. 6, 2002

(51) Int. Cl.[7] ..... A01H 5/00

(52) U.S. Cl. ..... Plt./317

(58) Field of Search ..... Plt./317, 319

*Primary Examiner*—Bruce R. Campell
*Assistant Examiner*—Annette H Para
(74) *Attorney, Agent, or Firm*—C. A. Whealy

(57) ABSTRACT

A new and distinct cultivar of Double Impatiens plant named 'Cameo Scarlet Surprise', characterized by its compact, mounded and outwardly spreading plant habit; rapid growth rate; freely branching habit; rounded dark green-colored leaves; densely foliated; freely flowering habit; fully double flower form; and large scarlet red and light pink bi-colored flowers that are positioned above and beyond the foliage.

1 Drawing Sheet

Botanical classification/cultivar designation: *Impatiens walleriana* cultivar Cameo Scarlet Surprise.

BACKGROUND OF THE INVENTION

The present invention relates to a new and distinct cultivar of Double Impatiens plant, botanically known as *Impatiens walleriana*, and hereinafter referred to by the cultivar name 'Cameo Scarlet Surprise'.

The new Impatiens is a product of a planned breeding program conducted by the Inventor in Cartago, Costa Rica. The objective of the breeding program was to develop new compact and mounded Double Impatiens cultivars with large fully double flowers, excellent branching, and interesting flower and foliage colors.

The new Impatiens originated from a cross made by the Inventor of two proprietary selections of *Impatiens walleriana*, not patented. The cultivar Cameo Scarlet Surprise was discovered and selected by the Inventor as a flowering plant within the progeny of the stated cross in a controlled environment in Cartago, Costa Rica.

Asexual reproduction of the new cultivar by terminal cuttings taken at Cartago, Costa Rica, since March, 2001, has shown that the unique features of this new Impatiens are stable and reproduced true to type in successive generations of asexual reproduction.

SUMMARY OF THE INVENTION

The following traits have been repeatedly observed and are determined to be the unique characteristics of 'Cameo Scarlet Surprise'. These characteristics in combination distinguish 'Cameo Scarlet Surprise' as a new and distinct cultivar:

1. Compact, mounded and outwardly spreading plant habit.
2. Rapid growth rate.
3. Freely branching habit.
4. Rounded dark green-colored leaves; densely foliated.
5. Freely flowering habit.
6. Fully double flower form.

7. Large scarlet red and light pink bi-colored flowers that are positioned above and beyond the foliage.

In side-by-side comparisons conducted in Cartago, Costa Rica, plants of the new Impatiens differed from plants of the female parent selection in the following characteristics:

1. Plants of the new Impatiens had larger leaves than plants of the female parent selection.
2. Plants of the new Impatiens had larger flowers than plants of the female parent selection.
3. Flowers of plants of the new Impatiens were scarlet red and light pink bi-colored whereas flowers of plants of the female parent selection were salmon and orange bi-colored.
4. Flowers of plants of the new Impatiens were fully double whereas flowers of plants of the female parent selection were semi-double.
5. Flowers of plants of the new Impatiens were sterile whereas flowers of plants of the female parent selection were fertile.

In side-by-side comparisons conducted in Cartago, Costa Rica, plants of the new Impatiens differed from plants of the male parent selection in the following characteristics:

1. Flowers of plants of the new Impatiens were scarlet red and light pink bi-colored whereas flowers of plants of the male parent selection were salmon and orange bi-colored.
2. Flowers of plants of the new Impatiens were fully double whereas flowers of plants of the male parent selection were semi-double.
3. Flowers of plants of the new Impatiens were sterile whereas flowers of plants of the male parent selection were fertile.

The new Impatiens can be compared to the *Impatiens walleriana* cultivar Fiesta Sparkler Red, not patented. However, in side-by-side comparisons conducted in Lompoc, Calif., plants of the new Impatiens differed from plants of the cultivar Fiesta Sparkler Red in the following characteristics:

1. Plants of the new Impatiens were mounded and outwardly spreading than plants of the cultivar Fiesta Sparkler Red which were more upright in plant habit.

2. Plants of the new Impatiens had larger leaves than plants of the cultivar Fiesta Sparkler Red.
3. Leaf under surfaces of plants of the new Impatiens were solid green in color whereas leaf under surfaces of plants of the cultivar Fiesta Sparkler Red were green with random purple-colored areas.
4. Plants of the new Impatiens had more petals per flower than plants of the cultivar Fiesta Sparkler Red.
5. Flowers of plants of the new Impatiens were scarlet red and light pink bi-colored whereas flowers of plants of the cultivar Fiesta Sparkler Red were orange red and white bi-colored.

The new Impatiens can be compared to the *Impatiens walleriana* cultivar Cameo Red Surprise, not patented. However, in side-by-side comparisons conducted in Lompoc, Calif., plants of the new Impatiens differed from plants of the cultivar Cameo Red Surprise in the following characteristics:

1. Plants of the new Impatiens were more compact than and not as vigorous as plants of the cultivar Cameo Red Surprise.
2. Leaf under surfaces of plants of the new Impatiens were solid green in color whereas leaf under surfaces of plants of the cultivar Cameo Red Surprise were green with random purple-colored areas.
3. Plants of the new Impatiens had smaller flowers with fewer petals per flower than plants of the cultivar Cameo Red Surprise.
4. Flowers of plants of the new Impatiens were scarlet red and light pink bi-colored whereas flowers of plants of the cultivar Cameo Red Surprise were scarlet red and white bi-colored.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens. The photograph comprises a side perspective view of a typical flowering plant of 'Cameo Scarlet Surprise' grown in a container.

DETAILED BOTANICAL DESCRIPTION

The cultivar Cameo Scarlet Surprise has not been observed under all possible environmental conditions. The phenotype may vary somewhat with variations in environment such as temperature and light intensity without, however, any variance in genotype.

The aforementioned photographs and following detailed botanical description describe plants grown in Lompoc, Calif., during the winter under commercial practice in a fiberglass-covered greenhouse with day temperatures about 21 to 24° C., night temperatures about 16 to 18° C. and light levels about 3,000 to 4,000 footcandles. Rooted cuttings were planted in 25-cm hanging basket containers and grown for about ten weeks.

In the following description, color references are made to The Royal Horticultural Society Colour Chart, 1995 Edition, except where general terms of ordinary dictionary significance are used.

Botanical classification: *Impatiens walleriana* cultivar Cameo Scarlet Surprise.

Parentage:

*Female parent.*—Proprietary selection of *Impatiens walleriana*, not patented.

*Male parent.*—Proprietary selection of *Impatiens walleriana*, not patented.

Propagation:

*Type cutting.*—Terminal cuttings.

*Time to initiate roots.*—Summer: About 10 days at 21° C. Winter: About 12 days at 21° C.

*Time to produce a rooted cutting.*—Summer and winter: About 21 days at 21° C.

*Root description.*—Fibrous, fine, white in color.

*Rooting habit.*—Freely branching, dense.

Plant description:

*General appearance.*—Compact, mounded and outwardly spreading. Appropriate for 10 to 15-cm pots and 20 and 25-cm hanging basket containers.

*Growth and branching habit.*—Vigorous and freely-branching with at least ten lateral branches developing towards the base, dense and bushy growth. Pinching, that is, removal of the terminal apices, is typically not required.

*Crop time.*—Relatively rapid growth rate. From planting one rooted cutting in a 10-cm pot: About five to six weeks. From planting three rooted cuttings in a 25-cm hanging basket container: About eight to ten weeks.

*Plant height.*—About 16 to 18 cm.

*Plant spread.*—About 25 cm.

*Lateral branches.*—Length: About 18 to 20 cm. Diameter: About 8 to 10 mm. Internode length: About 1 to 2 cm. Texture: Smooth, glabrous. Color: 147C.

*Foliage description.*—Arrangement: Alternate, simple; densely foliated. Length: About 4 to 4.5 cm. Width: About 3.5 to 4 cm. Shape: Ovate. Apex: Acute. Base: Acute to rounded. Margin: Slightly crenate with ciliation. Texture, upper and lower surfaces: Smooth, glabrous. Venation pattern: Pinnate. Color: Developing foliage, upper surface: 146A. Developing foliage, lower surface: 147C. Fully expanded foliage, upper surface: 147A. Fully expanded foliage, lower surface: 148B. Venation, upper surface: 147B. Venation, lower surface: 146A. Petiole: Length: About 1.2 to 1.5 cm. Diameter: About 3 mm. Texture, upper and lower surfaces: Smooth, glabrous. Color: 147C.

Flower description:

*Flower type and habit.*—Numerous and consistently double scarlet red and light pink bi-colored flowers. Freely and continuously flowering. Flower buds open similar to a rose in fullness; flowers rounded. Flowers arise from leaf axils. Usually about 8 to 15 flowers and flower buds per lateral branch. Flowers positioned above the foliage and typically face outward to upward. Flowers last about seven to ten days on the plant. Flowers not persistent. Flowers not fragrant.

*Flowering season.*—Year-round under greenhouse conditions. In the garden, flowering is continuous from spring until fall.

*Flower diameter.*—About 4 cm.

*Flower depth (height).*—About 2 cm.

*Flower buds.*—Rate of opening: From showing color to fully open flower, about five to seven days is typical depending on temperature. Length: About 1 to 1.5 cm. Diameter: About 1.2 cm. Shape: Ovoid. Color, before showing petal color: 146D.

*Petals.*—Quantity/arrangement: About 25 to 30 per flower; imbricate. Length, outer petals: About 2.5 cm. Width, outer petals: About 2 cm. Shape: Cordate to ovate. Apex: Rounded or emarginate. Base: Acute. Margin: Entire; slightly ruffled. Texture, upper and lower surfaces: Smooth, glabrous. Color: When opening and fully opened, upper surface: Towards margin, light pink, 56D; towards center, scarlet red, 45B. With development, light pink areas become larger. When opening and fully opened, lower surface: Towards margin, light pink, 56D; towards center, scarlet red, 43C. With development, light pink areas become larger.

*Peduncles.*—Length: About 2.5 to 3 cm. Diameter: Less than 1 mm. Angle: About 45° to the lateral branch. Strength: Strong; flexible. Color: 148B.

*Reproductive organs.*—None observed.

*Fruit/seed.*—Production of fruit and seed has not been observed.

Disease/pest resistance: Plants of the new Impatiens have demonstrated good resistance to pathogens common to Impatiens, such as Botrytis. Plants of the new Impatiens have not been observed to be resistant to pests common to Impatiens.

Weather tolerance: Plants of the new Impatiens have been observed to be tolerant to rain, wind and temperatures ranging from 5 to 38° C.

It is claimed:

1. A new and distinct cultivar of Double Impatiens plant named 'Cameo Scarlet Surprise', as illustrated and described.

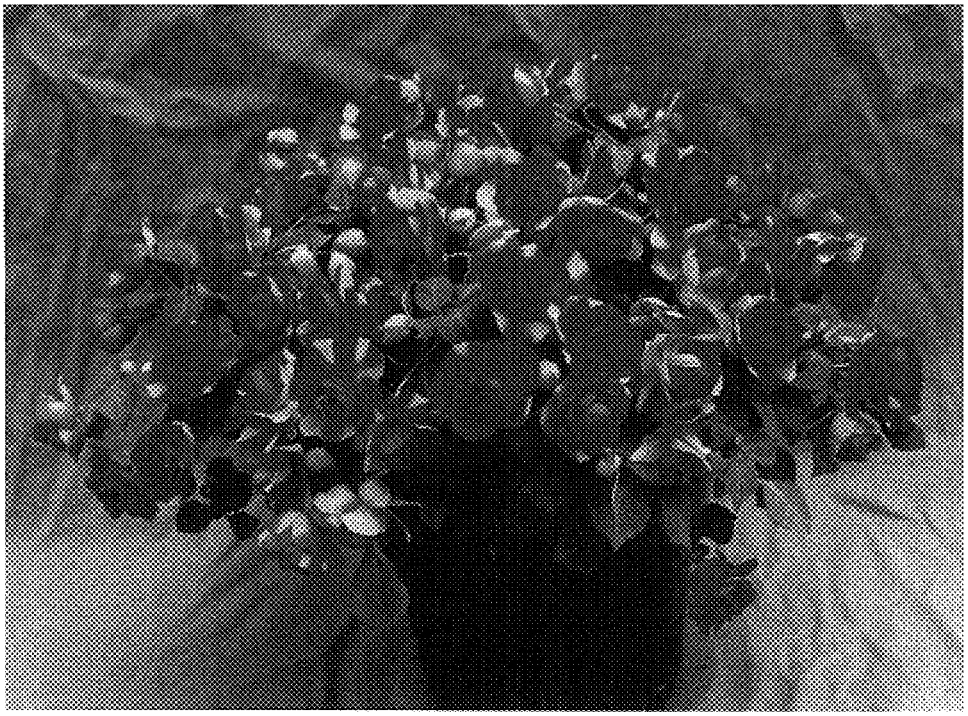

* * * * *